(12) United States Patent
Oono et al.

(10) Patent No.: US 10,209,228 B2
(45) Date of Patent: Feb. 19, 2019

(54) ULTRASONIC TESTING DEVICE AND ULTRASONIC TESTING METHOD

(71) Applicant: Hitachi Power Solutions Co., Ltd., Hitachi-shi, Ibaraki (JP)

(72) Inventors: Shigeru Oono, Hitachi (JP); Kenta Sumikawa, Hitachi (JP)

(73) Assignee: Hitachi Power Solutions Co., Ltd., Hitachi-shi (JP)

( * ) Notice: Subject to any disclaimer, the term of this patent is extended or adjusted under 35 U.S.C. 154(b) by 160 days.

(21) Appl. No.: 15/116,886

(22) PCT Filed: Jan. 30, 2015

(86) PCT No.: PCT/JP2015/052750
§ 371 (c)(1),
(2) Date: Aug. 5, 2016

(87) PCT Pub. No.: WO2015/119063
PCT Pub. Date: Aug. 13, 2015

(65) Prior Publication Data
US 2017/0176397 A1    Jun. 22, 2017

(30) Foreign Application Priority Data
Feb. 6, 2014    (JP) .................................. 2014-020907

(51) Int. Cl.
*G01N 29/24*    (2006.01)
*G01N 29/26*    (2006.01)
(Continued)

(52) U.S. Cl.
CPC ........... *G01N 29/28* (2013.01); *G01N 29/225* (2013.01); *G01N 29/2487* (2013.01);
(Continued)

(58) Field of Classification Search
CPC .. G01N 29/28; G01N 29/225; G01N 29/2487; G01N 29/262; G01N 2291/106; G01N 2291/0289; G01N 2291/2632
(Continued)

(56) References Cited

U.S. PATENT DOCUMENTS 4,507,969 A * 4/1985 Djordjevic ............. G01N 29/28
73/644
7,530,271 B2 * 5/2009 Busch .................. G01N 29/225
73/618
(Continued)

FOREIGN PATENT DOCUMENTS

JP    5-232093 A    9/1993
JP    9-133663 A    5/1997
(Continued)

OTHER PUBLICATIONS

International Search Report (PCT/ISA/210) issued in PCT Application No. PCT/JP2015/052750 dated Apr. 28, 2015 with English-language translation (four (4) pages).
(Continued)

*Primary Examiner* — J M Saint Surin
(74) *Attorney, Agent, or Firm* — Crowell & Moring LLP

(57) ABSTRACT

The invention is applied to an ultrasound inspection apparatus including an array probe such that wetting is substantially limited to an inspection surface of the work. The ultrasound inspection apparatus includes: a work holder that holds a work with an inspection surface thereof facing downward; an array probe that probes the work with an ultrasonic wave; a water tank in which the array probe is immersed in water; an arm that holds the array probe such that the array probe faces an underside of the inspection surface of the work; X-axial direction scanning means that horizontally scans the work, with a liquid surface coming into contact with the inspection surface of the work due to
(Continued)

surface tension of a liquid stored in the water tank; and Y-axial direction scanning means that horizontally scans the array probe.

8 Claims, 6 Drawing Sheets

(51) Int. Cl.
*G01N 29/22* (2006.01)
*G01N 29/28* (2006.01)

(52) U.S. Cl.
CPC ... *G01N 29/262* (2013.01); *G01N 2291/0289* (2013.01); *G01N 2291/106* (2013.01); *G01N 2291/2632* (2013.01)

(58) Field of Classification Search
USPC .......................................................... 73/625
See application file for complete search history.

(56) References Cited

U.S. PATENT DOCUMENTS

| | | | | |
|---|---|---|---|---|
| 7,571,649 | B2 * | 8/2009 | Young | G01N 29/225 73/635 |
| 7,661,315 | B2 | 2/2010 | Busch et al. | |
| 7,917,317 | B2 * | 3/2011 | McKeon | G01N 29/043 702/171 |
| 8,151,645 | B2 * | 4/2012 | Vivek | B41J 2/005 73/644 |
| 8,459,120 | B2 * | 6/2013 | Keeton | G01N 29/223 73/618 |
| 8,720,273 | B2 * | 5/2014 | Kessler | G01N 29/0681 73/606 |
| 2005/0257617 | A1 | 11/2005 | Busch et al. | |
| 2011/0283799 | A1 * | 11/2011 | De Odorico | G01N 29/225 73/644 |
| 2013/0276540 | A1 | 10/2013 | Fujiwara et al. | |

FOREIGN PATENT DOCUMENTS

| | | |
|---|---|---|
| JP | 2007-315881 A | 12/2007 |
| JP | 2009276319 * | 11/2009 |
| JP | 2012-58077 A | 3/2012 |
| JP | 2014-6177 A | 1/2014 |
| JP | 5650339 B1 | 1/2015 |
| KR | 10-2014-0001138 A | 1/2014 |

OTHER PUBLICATIONS

Japanese-language Written Opinion (PCT/ISA/237) issued in PCT Application No. PCT/JP2051/052750 dated Apr. 28, 2015 (five (5) pages).

* cited by examiner

[Fig.1]
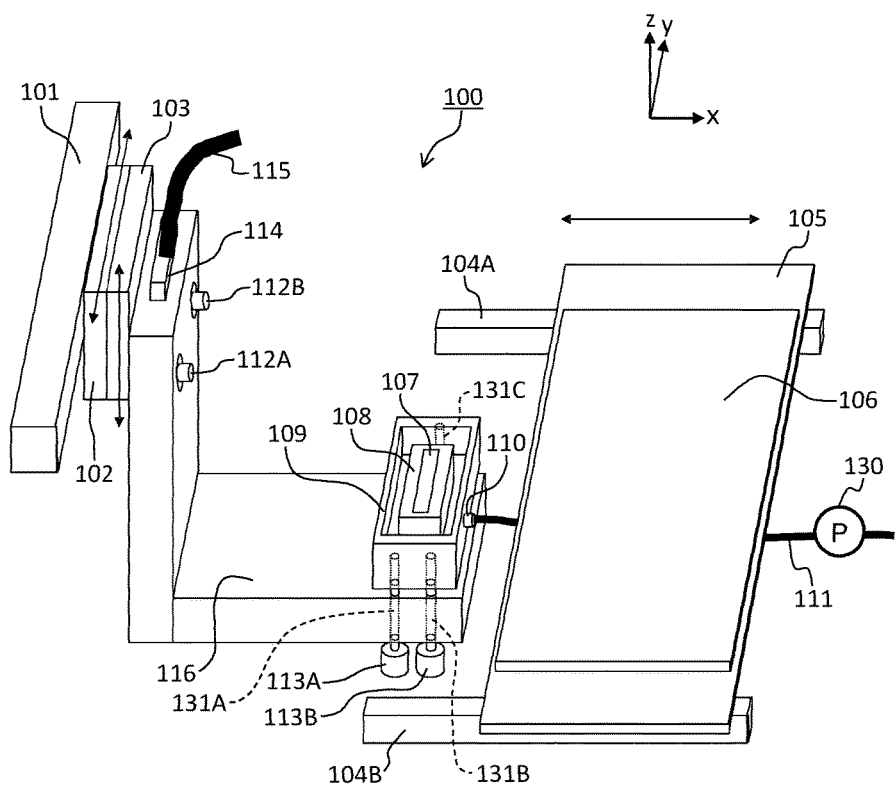

【Fig.2】
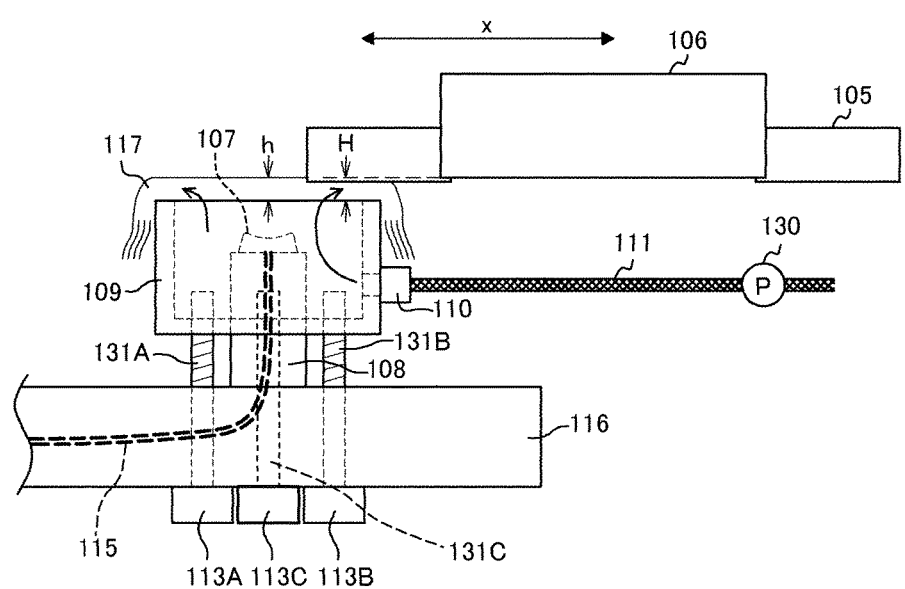

[Fig.3]
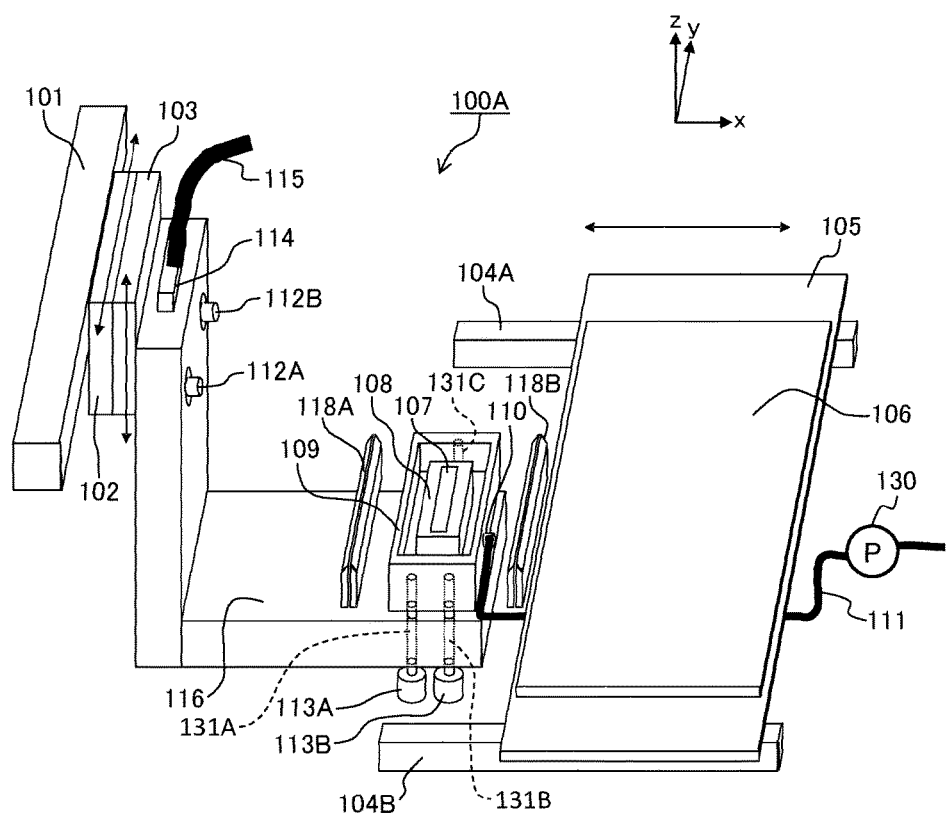

[Fig.4]
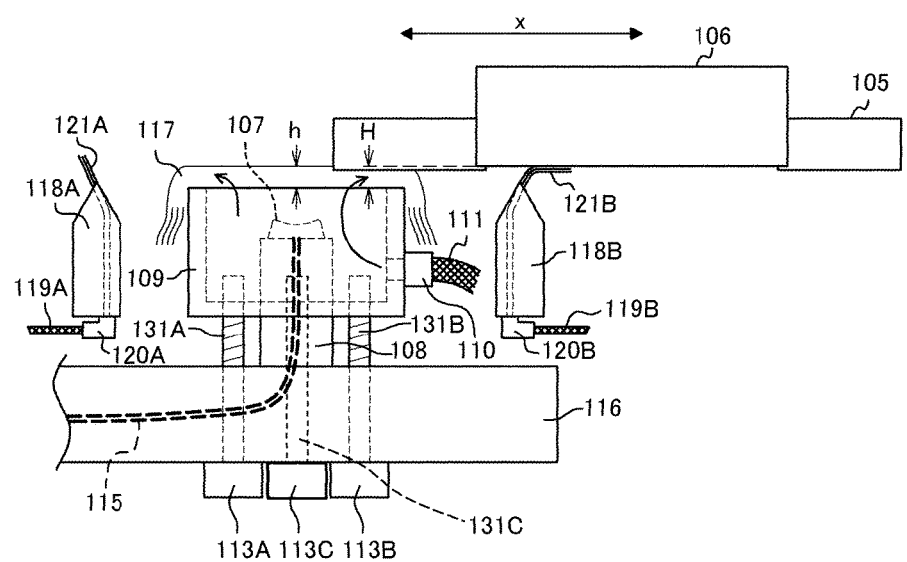

[Fig.5]
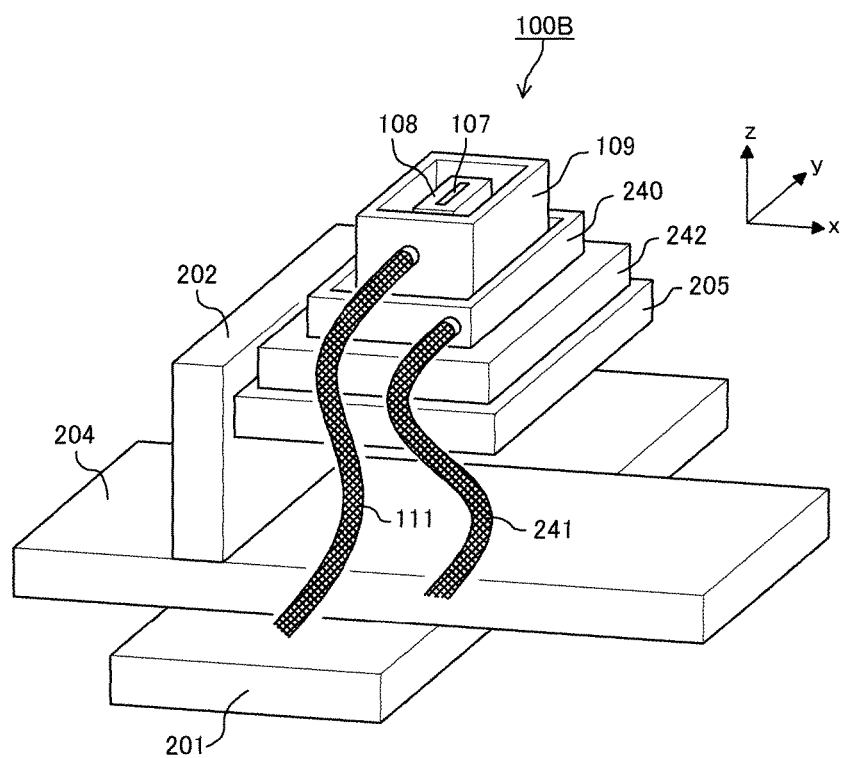

[Fig.6]
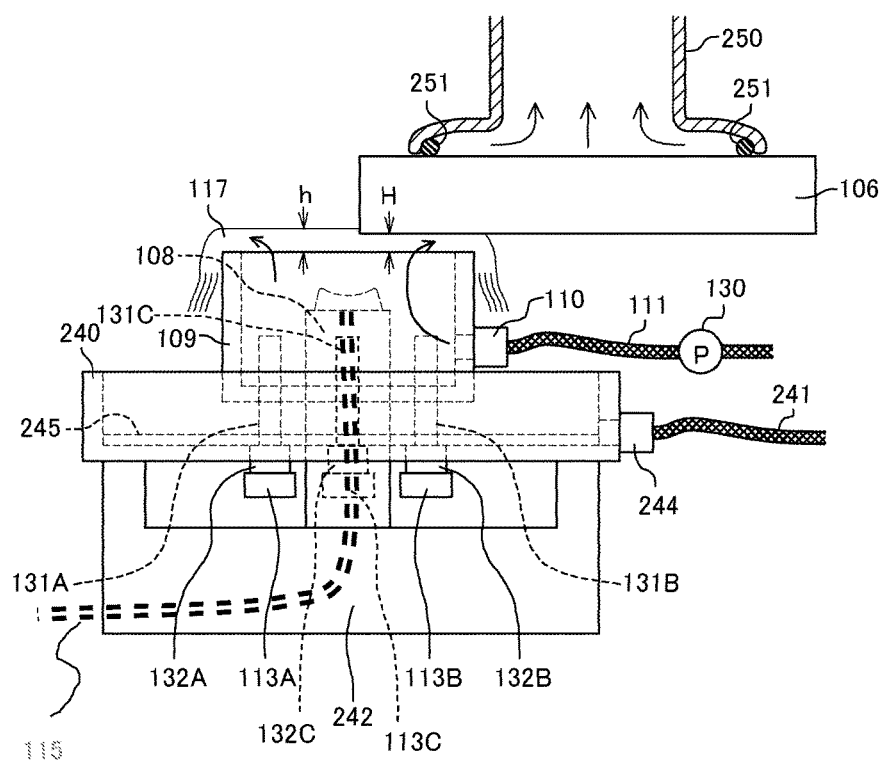

ULTRASONIC TESTING DEVICE AND ULTRASONIC TESTING METHOD

TECHNICAL FIELD

The present invention relates to an ultrasound inspection apparatus and an ultrasound inspection method.

BACKGROUND ART

An ultrasound inspection apparatus irradiates a subject (hereinafter, referred to as a "work" in some cases) as an inspection object with an ultrasound wave, receives a reflected or transmitted ultrasound wave using an ultrasound probe (hereinafter, referred to as a "probe" in some cases), and forms an image. For example, in a case where the work is an electronic device, there is a need to detect a minute defect, and thus the ultrasound inspection apparatus needs to have high resolution. When the ultrasound inspection apparatus uses a high-frequency ultrasound wave, high resolution is achieved; on the other hand, there is a concern that attenuation of the ultrasound wave will be increased and thus, an S/N ratio will be lowered. Since the ultrasound wave is attenuated in water less than in air, normally, the work is immersed in water and ultrasound inspection is often performed, with water filled between the tip of the probe and a surface of the work. The ultrasound inspection apparatus focuses on an interface in the work as an observation target, scans the probe, and forms an image of the obtained result, while a distance (hereinafter, referred to as a "water distance" in some cases) between the tip of the probe and the surface of the work is maintained to be a predetermined value,. In this manner, a position, a shape, and a depth of the defect can be found.

Wetting the electronic device in water results in failure such as corrosion or metallic contamination. Therefore, in the related art, sampling inspection has been performed for ultrasound inspection of the electronic device. However, only one defect in an in-vehicle electronic device or the like results in a significant loss in some cases. There is a growing need for 100% inspection such that even one defect does not occur after shipment. In other words, in the inspection of such an important component, there is a need to avoid wetting as much as possible and to perform the inspection at a high speed.

The ultrasound probe is broadly divided into a single probe in which one ultrasonic vibration element is disposed, and an array probed in which multiple ultrasonic vibration elements are arranged in a row. The single probe performs transmission and reception of the ultrasound wave using the single ultrasonic vibration element. The array probe transmits and receives one ultrasonic pulse beam with a plurality of groups of ultrasonic vibration elements arranged in a row, in which the group is formed of a few ultrasonic vibration elements which are connected to each other.

The ultrasound inspection apparatus including the array probe transmits a wave transmitting signal (excitation signal) to each of the ultrasonic vibration elements constituting the plurality of groups of ultrasonic vibration elements. The ultrasound inspection apparatus further receives a wave receiving signal (echo wave receiving signal) from each of the ultrasonic vibrators. The ultrasound inspection apparatus applies a predetermined time lag (delay pattern) to the wave transmitting signal (excitation signal) and the wave receiving signal (echo wave receiving signal), and causes the elements to function as a so-called phased array. In this manner, the ultrasound inspection apparatus can concentrate an ultrasonic beam to a focus and can obtain an ultrasonic echo having a focal point. Curvature is applied in a direction orthogonal to an arrangement direction of the ultrasonic vibration elements, thereby making it possible to concentrate the ultrasonic beam to the focus also in the direction orthogonal to the arrangement direction such that the ultrasonic echo having a focal point is obtained. In the array probe, the plurality of groups of ultrasonic vibrators that transmits the ultrasonic pulse beams are electronically scanned, thereby making it possible to perform measurement at a high speed. In a case of inspecting a large work such as an insulated gate bipolar transistor (IGBT) or a silicon wafer, the array probe is used to increase throughput in some cases.

In a case of inspecting a work such as an electronic device that is vulnerable to water, as shown in FIG. 1 in PTL 1, there is proposed a type of local-immersion probe, which is disposed below a work having an inspection surface facing downward and suctions up water around the probe. On page 8 in PTL 1, the following description is provided. "As shown in FIG. 1, acoustic coupling of the ultrasonic beam to the wafer is enhanced by a column of water or other fluid 110 that is maintained by flowing fluid from one or more positions in close proximity to the transducer."

CITATION LIST

Patent Literature

PTL 1: U.S. Pat. No. 7,661,315

SUMMARY OF INVENTION

Technical Problem

However, since the probe disclosed in PTL 1 has a shape in which an ultrasound emission surface projects on an outlet of water, there is a need to form a column of water at a predetermined water pressure. Particularly, in a case where a water distance between the ultrasound emission surface of the probe to an inspection surface is long, high water pressure is needed. Therefore, foam (cavitation) is likely to be generated due to a rapid change in the water pressure in the vicinity of the water outlet of the probe or at a position at which the column of water hits the inspection surface of the work. Such foam results in significant attenuation in a high-frequency ultrasonic wave and thus, is an obstacle in inspection.

A method disclosed in PTL 1 can be applied to a single probe which may operate with a thin column of water; however, it is difficult for the method to be applied to an array probe which needs to form a thick column of water and to maintain uniform and stable distribution of water pressure over a broad area.

In general, the ultrasound inspection apparatus is used to inspect a defect not on the front surface of the work, but in the work. Therefore, it is normal that the water distance is used in a state of being shorter than a focal length of the probe, and a depth, at which the ultrasound inspection apparatus focuses on the work, also varies depending on a material of the work or a structure of the work in a depth direction. In addition, in a work having a multi-layer structure, in a case of achieving a detailed evaluation of a defect in each layer, there is a need to perform inspection a plurality of times by changing the water distance. Thus, in the method in PTL 1, it is difficult to focus on a portion of the work at a predetermined depth according to types of works.

In addition, there has been proposed a type of local-immersion probe which is disposed above a work having an inspection surface facing upward, and water is supplied from above the probe. In this method, it is possible to further reduce an area of a wet portion than in a method in which a work is completely immersed; however, there is a concern that water flows around to a part of a side surface or the bottom of an inspection object.

Hence, an object of the present invention is that the invention is applied to an ultrasound inspection apparatus including an array probe and an ultrasound inspection method thereof such that it is possible to inspect a work having a multi-layer structure and wetting is substantially limited to an inspection surface of the work.

Solution to Problem

In order to achieve the above object, an ultrasound inspection apparatus according to a first aspect of the invention includes: a subject holding mechanism that holds a subject with an inspection surface thereof facing downward; an array probe that probes the subject with an ultrasonic wave; a tank in which the array probe is immersed in a liquid that causes ultrasonic waves to be propagated; a probe holding mechanism that holds the array probe such that the array probe faces an underside of the inspection surface of the subject; and horizontal scanning means that horizontally scans the subject and/or the array probe, with a liquid surface coming into contact with the inspection surface of the subject due to surface tension of a liquid stored in the tank.

An ultrasound inspection apparatus according to a second aspect of the invention includes: a subject holding mechanism that holds a subject with an inspection surface thereof facing downward; an array probe that probes the subject with an ultrasonic wave; a tank in which the array probe is immersed in a liquid that causes ultrasonic waves to be propagated; a probe holding mechanism that holds both the array probe and the tank such that the array probe faces an underside of the inspection surface of the subject; horizontal scanning means that horizontally scans the subject and/or the array probe, with a liquid surface coming into contact with the inspection surface of the subject due to surface tension of a liquid stored in the tank; and a height adjusting mechanism that can change, individually, a distance between the array probe and the inspection surface of the subject, and a distance between the top edge of the tank in which the array probe is immersed and the inspection surface of the subject.

An ultrasound inspection method according to the first aspect of the invention performs: a step of holding a subject with an inspection surface thereof facing downward; a step of supplying a liquid, which causes ultrasonic waves to be propagated, into a tank surrounding an array probe held below the inspection surface of the subject, and of causing a liquid surface of the liquid to be higher than a top edge of the tank due to surface tension; and a step of horizontally scanning the subject and/or the array probe, with a liquid surface coming into contact with the inspection surface of the subject due to surface tension of a liquid stored in the tank.

An ultrasound inspection method according to the second aspect of the invention performs: a step of holding a subject with an inspection surface thereof facing downward; a step of adjusting a distance between an array probe and the inspection surface of the subject; a step of supplying a liquid, which causes ultrasonic waves to be propagated, into a tank surrounding the array probe held below the inspection surface of the subject, and of causing a liquid surface of the liquid to be higher than a top edge of the tank due to surface tension; a step of focusing on a layer on which inspection is to be performed, with the liquid surface coming into contact with the inspection surface of the subject due to the surface tension of the liquid stored in the tank; and a step of horizontally scanning the subject and/or the array probe. Another type of means is described in Description of Embodiments.

Advantageous Effects of Invention

According to the present invention, the invention is applied to an ultrasound inspection apparatus including an array probe and an ultrasound inspection method thereof such that it is possible to inspect a work having a multi-layer structure and wetting is substantially limited to an inspection surface of the work.

BRIEF DESCRIPTION OF DRAWINGS

FIG. 1 is a view of a schematic configuration showing an ultrasound inspection apparatus according to a first embodiment.

FIG. 2 is an enlarged view showing a configuration in the vicinity of an array probe and an operation thereof according to the first embodiment.

FIG. 3 is a view of a schematic configuration showing an ultrasound inspection apparatus according to a second embodiment.

FIG. 4 is an enlarged view showing a configuration in the vicinity of an array probe and an operation thereof according to the second embodiment.

FIG. 5 is a view of a schematic configuration showing a part of an ultrasound inspection apparatus according to a third embodiment.

FIG. 6 is an enlarged view showing a configuration in the vicinity of an array probe and an operation thereof according to the third embodiment.

DESCRIPTION OF EMBODIMENTS

Hereinafter, embodiments of the present invention will be described with reference to the drawings.

First Embodiment

FIG. 1 is a view of a schematic configuration showing an ultrasound inspection apparatus 100 according to a first embodiment.

As shown in FIG. 1, the ultrasound inspection apparatus 100 includes a work holder 105 (subject holding mechanism) that holds a work 106 (subject) with an inspection surface thereof facing downward, X-axial direction scanning means 104A and 104B (horizontal scanning means) that enables the work holder to move in a horizontal (X-axial) direction. Further, the ultrasound inspection apparatus 100 includes an arm 116, a stage 103 to which the arm 116 is fixed, and Y-axial direction scanning means 101 and Z-axial direction scanning means 102 that enable the stage 103 to move.

The work 106 has a multi-layer structure and thus, needs to be inspected at a predetermined depth from the inspection surface.

The arm 116 (probe holding mechanism) holds the array probe 107, a casing 108 of the probe, and a water tank 109 on an upper side of the arm. The arm 116 holds the casing 108 of the array probe 107 such that the array probe 107 faces an underside of the inspection surface of the work 106. Further, the arm 116 includes a connector 114 in its upper portion. A signal cable 115 of an external signal processing device is connected to the connector 114. The signal cable 115 causes the array probe 107 to generate an ultrasonic wave, or detects an ultrasonic wave that returns after being reflected from the work 106.

The Y-axial direction scanning means 101 (horizontal scanning means) enables the stage 103 to move in the horizontal (Y-axial) direction, thereby scanning the inspection surface of the work 106 by the array probe 107 in the horizontal (Y-axial) direction. Note that the horizontal scanning means is not limited to the first embodiment and may horizontally scan the work 106 and/or the array probe 107. In this manner, the horizontal scanning means can relatively scan the array probe 107 with respect to the inspection surface of the work 106.

The Z-axial direction scanning means 102 enables the stage 103 to move in a height (Z-axial) direction, thereby enabling the water tank 109 and the array probe 107 on the arm 116 to move in the height direction. The Z-axial direction scanning means 102 is an example of a height adjusting mechanism that adjusts relative heights of the array probe 107 and the water tank 109 with respect to the inspection surface of the work 106. In addition, the Z-axial direction scanning means 102 is also used to concentrate, to a focus, an ultrasonic wave with which irradiation is performed.

The array probe 107 is disposed so as to have its longitudinal direction parallel to the Y-axial direction. The water tank 109 (tank) is provided around the array probe 107 and the casing 108. In the water tank 109, water is stored such that the array probe 107 and the casing 108 are immersed in water. A water surface comes into contact with the inspection surface of the work 106 due to surface tension of water stored in the water tank 109. In this manner, since a space between the inspection surface and the array probe 107 is filled with water, the array probe 107 can probe the work 106 with an ultrasonic wave. Note that a substance that fills the space between the inspection surface and the array probe 107 is not limited to water, and any liquid can be used as long as ultrasonic waves can be propagated in the liquid.

Since the space between the inspection surface and the array probe 107 is reliably filled with water, an outer edge of the water tank 109 may be wider than an outer edge of the array probe 107 by 5 mm or greater. A water supply port 110, and a water supply tube 111 that is connected to the water supply port 110 are provided on a side surface of the water tank 109. A pump 130 that supplies water to the water tank 109 is connected to the water supply tube 111. The pump 130 supplies an amount of water into the water tank 109 to the extent that no ripple is formed on a liquid surface of water 117 accumulated in the water tank 109. The pump 130 can perform flow-rate regulation. However, the configuration is not limited thereto, and the pump that supplies a predetermined flow rate, and a flow-rate regulating mechanism, in which ha valve, which can regulate a flow path, and a bypass tube are incorporated, may supply an amount of water to the extent that no ripple is formed on the liquid surface of the water tank 109.

The water tank 109 is supported by adjustment screws 131A, 131B, and 131C, and attached to the casing 108 of the array probe 107 by being fitted to the casing to the extent without the water tank moves vertically in a smooth manner without rattling. Since the adjustment screws 131A, 131B, and 131C are not involved in fixing of or adjusting a position of the array probe 107, parallelization and height adjustment of the top edge of the water tank 109 can be performed separately form the height adjustment and parallelization of the array probe 107. The adjustment screws 131A, 131B, 131C are connected to adjustment knobs 113A and 113B and an adjustment knob (not shown), respectively. The adjustment knobs 113A and 113B and the adjustment knob (not shown) have the same amount of feeding, thereby making it possible to perform the height adjustment of the top edge of the water tank 109. Further, the amount of the feeding of the adjustment knobs 113A and 113B and an adjustment knob 113C (refer to FIG. 2) are minutely changed, respectively, making it possible to perform fine adjustment such that a surface of the water 117 stored in the water tank 109 is substantially parallel to the inspection surface.

As described above, the water tank 109 is attached to the casing 108 of the array probe 107 by being fitted to the casing to the extent that the water tank moves vertically in a smooth manner without rattling. Therefore, a large amount of water does not leak from a space between the water tank 109 and the casing 108. Note that sealing may be performed between the water tank 109 and the casing 108 with an O-ring or the like as necessary. The adjustment screws 131A, 131B, and 131C and the adjustment knobs 113A and 113B and the adjustment knob 113C (refer to FIG. 2) are examples of the height adjustment mechanism that adjusts the relative height of the water tank 109 with respect to the inspection surface of the work 106.

When the inspection is performed using the array probe 107, the array probe 107 needs to be disposed to have the longitudinal direction of the array probe 107 substantially parallel to the inspection surface of the work 106. Inclination (amount of tilting) of the array probe 107 (casing 108) in the longitudinal direction can be adjusted by the fixing screws 112A and 112B.

The fixing screws 112A and 112B fix the arm 116, which holds the array probe 107, to the stage 103. The fixing screws 112A and 112B pass though elongated holes.

A position at which the arm 116 is fixed to the stage 103 can be adjusted by adjusting positions of the elongated holes in which the fixing screws 112A and 112B are stopped. Accordingly, it is possible to adjust the amount of tilting of the array probe 107 and to be disposed to be parallel to the inspection surface of the work 106. In other words, the fixing screws 112A and 112B are tilting-amount adjusting mechanism that adjusts the amount of the tilting of the array probe 107.

The ultrasound inspection apparatus 100 of the first embodiment performs the inspection as follows.

As shown in FIG. 1, the work 106 with the horizontal inspection surface facing downward is positioned on the work holder 105. At this time, chucking is performed as necessary. In a method of chucking in the first embodiment, the work 106 is mechanically stopped on the work holder 105 by supporting the work 106 from below. As another method different from the above method, a method of holding the work 106 by performing vacuum suction on the top surface of the work, or a method of holding the work 106 from the side surfaces by pressing a material having a high friction coefficient against side surfaces of the work are considered. In this manner, the inspection surface of the work 106 horizontally faces downward.

Next, the inspector causes the array probe 107 to move to a position below the inspection surface (inspection region) of the work 106, using the X-axial direction scanning means 104A and 104B and the Y-axial direction scanning means 101.

Next, the pump 130 supplies water to the water tank 109 through the water supply tube 111 and the water supply port 110 and time is taken for the water 117 to overflow the top edge of the water tank 109. In this manner, it is possible for the liquid surface to be higher than the top edge of the water tank 109 due to the surface tension of water. The pump 130 supplies water to the extent that no ripple is formed on the water surface and the water surface appears to be substantially a still-water surface. This is done so as to prevent an ultrasonic wave generated from the array probe 107 from being readily reflected from bubbles generated when a ripple is formed on the water surface.

FIG. 2 is an enlarged view showing a configuration in the vicinity of the array probe 107 and an operation thereof according to the first embodiment, in which the water 117 overflows the edge of the water tank 109.

As shown in FIG. 2, the water surface of the water 117 is raised by a height h from the top edge of the water tank 109 due to the surface tension.

In this state, the array probe 107 and the water tank 109 are lifted by using the Z-axial direction scanning means 102 until the liquid surface of the water 117 reaches the inspection surface. At this time, when the position of the top edge of the water tank 109 is too high or reaches the inspection surface of the work 106 by being inclined, the inclination is adjusted by using the adjustment knobs 113A, 113B, and 113C. In this manner, it is possible to perform height adjustment (distance adjustment) and parallelization of the top edge of the water tank 109.

As shown in FIG. 2, the signal cable 115 is electrically connected to the array probe 107 through the inside of the arm 116. The signal cable 115 passes through the inside of the arm 116, and a space between the array probe 107 and the casing 108 and a space between the casing 108 and the arm 116 are filled with caulking or the like, thereby preventing short due to wetting of the signal cable.

Hereinafter, a method of inspection will be described also with reference to FIG. 1.

The inspector causes an ultrasonic wave to be generated from the array probe 107 connected to the signal cable 115 and to focus on the inspection surface of the work 106. The Z-axial direction scanning means 102 is used to concentrate the ultrasonic wave to the focus. At this time, a height of the water tank 109 is also adjusted appropriately by using the adjustment knobs 113A, 113B, and 113C, depending on movement of the Z-axial direction scanning means 102 such that the top edge of the water tank 109 does not collide with the work, or the surface of the water 117 is not separated from the inspection surface. The fixing screws 112A and 112B are adjusted such that time taken for an echo signal reflected from the inspection surface of the work 106 to return is uniformly taken for the array probe 107 in the longitudinal direction, and thereby parallelization of the array probe 107 is performed with respect to the inspection surface of the work 106. In this manner, the array probe 107 can probe a surface parallel to the inspection surface of the work 106 with the ultrasonic wave.

Then, using the Z-axial direction scanning means 102, the inspector focuses the array probe 107 on a predetermined depth at which the inspection of the work 106 needs to be performed. At this time, the inspector also adjusts a height of the water tank 109 appropriately by using the adjustment knobs 113A, 113B, and 113C, depending on the movement of the Z-axial direction scanning means 102 such that the top edge of the water tank 109 does not collide with the work, or the surface of the water 117 is not separated from the inspection surface. Further, the height adjustment (distance adjustment) and the parallelization of the water tank 109 are performed by using the adjustment knobs 113A, 113B, and 113C such that a height H is secured between the edge of the water tank 109 and the inspection surface. In this manner, the ultrasound inspection apparatus 100 can inspect a layer at a predetermined depth from the inspection surface of the work 106.

As shown in FIG. 2, the height H of the inspection surface of the work 106 with respect to the top edge of the water tank 109 is equal to or smaller than a height h of the water surface raised from the top edge of the water tank 109 due to the surface tension. In this manner, in the state in which the water surface appears to be substantially the still-water surface without a ripple, it is possible for the liquid surface of the water 117 to come into contact with the inspection surface and thus, it is possible to reduce an occurrence of bubbles. Here, the height H is set to be greater than 0 mm and 2 mm or less. With the operations described above, the adjustment of the array probe 107 and the water tank 109 is completed.

It is desirable that a surface of the top edge of the water tank 109 facing the inspection surface is formed of a material having poor wettability with respect to water or a material subjected to surface processing so as to have poor wettability, because the height h of the water surface raised from the top edge of the water tank 109 is increased due to the surface tension.

Next, the ultrasound inspection apparatus 100 causes the array probe 107 to move to a starting point and scanning is started.

First, the X-axial direction scanning means 104A and 104B horizontally scan the work 106 in the X direction by sending the work in the X direction. The X-axial direction scanning means 104A and 104B (horizontal scanning means) scan the work 106 in the horizontal (X-axial) direction, with the liquid surface coming into contact with the inspection surface of the work 106 due to the surface tension of the water stored in the water tank 109.

When scanning of one line in the X direction is completed, the Y-axial direction scanning means 101 sends the array probe 107 by an amount of a length of the array probe 107 in the longitudinal direction. The Y-axial direction scanning means 101 (horizontal scanning means) sends the work 106 in the horizontal (Y axis) direction, with the liquid surface coming into contact with the inspection surface of the work 106 due to the surface tension of the water stored in the water tank 109.

Next, the X-axial direction scanning means 104A and 104B send the work 106 horizontally in a direction opposite to the previous scanning in the X direction. The X-axial direction scanning means 104A and 104B (horizontal scanning means) scans the work 106 in the horizontal direction, with the liquid surface coming into contact with the inspection surface of the work 106 due to the surface tension of the water stored in the water tank 109.

The ultrasound inspection apparatus 100 repeats the scanning procedures and scans the inspection region. After the completion of the scanning of the inspection region, scanning is again performed by focusing on a layer of the work 106 at another depth in accordance with the above procedure as necessary. In this manner, the ultrasound inspection apparatus 100 can scan the work 106 having the multi-layer structure.

The scanning of the array probe 107 by the Y-axial direction scanning means 101 is performed at a speed which is slow to the extent that no air enters the space between the inspection surface of the work 106 and the water tank 109.

In this manner, the bubbles are prevented from being put on the inspection surface so as not to be an obstacle to the irradiation and reception of the ultrasonic wave by the array probe 107.

Second Embodiment

In a second embodiment, air-current generators that generate a sheet-shaped air current are provided before and after the array probe 107 in the scanning direction, an air current is blown out to the wet inspection surface by contact with the water so as to dry the inspection surface, and the scanning is performed. In this manner, it is possible to prevent an adverse effect due to the wetting of the work 106 in water.

FIG. 3 is a view of a schematic configuration showing an ultrasound inspection apparatus 100A according to the second embodiment. The same reference signs are assigned to the same components as those in the ultrasound inspection apparatus 100 of the first embodiment shown in FIG. 1.

As shown in FIG. 3, the ultrasound inspection apparatus 100A of the second embodiment is provided with air knife generators 118A and 118B (air-current generators), in addition to the same configuration as the ultrasound inspection apparatus 100 of the first embodiment.

The air knife generators 118A and 118B (air-current generators) are provided before and after the array probe 107 in a transverse direction thereof so as to be parallel to the array probe 107. The air knife generators 118A and 118B generate a sheet-shaped air current in a direction of being away from the water tank 109. The sheet-shaped air current is referred to as an air knife in some cases.

In the air knife generators 118A and 118B, a high-pressure gas having a pressure of 0.1 [MPa] or higher, such as dry air or dry hydrogen, is supplied though a gap tube. The air knife generators 118A and 118B blows out a high-pressure gas from a gap of a slit so as to form a sheet shape.

The ultrasound inspection apparatus 100A blow off, by an air knife, the water remaining on the inspection surface of the work 106, after passing of the array probe 107. In this manner, it is possible to still further prevent an adverse effect due to the wetting of the work 106 in water. The air knife generating devices 118A and 118B may include a heating unit and may blow out a sheet-shaped air current as hot air. It is possible to improve effects of the drying by the air knife of the hot air.

FIG. 4 is an enlarged view showing a configuration in the vicinity of the array probe 107 and an operation thereof according to the second embodiment. The same reference signs are assigned to the same components as those in the first embodiment shown in FIG. 2. An example shown in FIG. 4 represents a state in which water droplets remaining on the inspection surface of the work 106 is blown off by an air knife current 121B in a case where the work 106 is scanned from left to right in the drawing.

The air knife generator 118A includes a high-pressure gas supply port 120A. A high-pressure gas tube 119A is connected to the high-pressure gas supply port 120A. The high-pressure gas is supplied to the air knife generator 118A from the high-pressure gas supply port 120A through the high-pressure gas tube 119A, and is blown out upward in an oblique leftward direction as an air knife current 121A so as to have a sheet shape.

Similarly, the air knife generator 118B includes a high-pressure gas supply port 120B. A high-pressure gas tube 119B is connected to the high-pressure gas supply port 120B. The high-pressure gas is supplied to the air knife generator 118B from the high-pressure gas supply port 120B through the high-pressure gas tube 119B, and is blown out downward in an oblique rightward direction as an air knife current 121B so as to have a sheet shape.

The intervals of the slits in the air knife generators 118A and 118B are formed in an oblique direction of being away from the water tank 109 with respect to the inspection surface. In this manner, the sheet-shaped air current (air knife) is blown toward the inspection surface so as to blow off water remaining on the inspection surface of the work 106, and is blown in an oblique direction of being away from the water tank 109. In this manner, it is possible to maintain stability of the water surface in the water tank 109 without a ripple.

When the sheet-shaped air current (air knife) is blown in a perpendicular direction or in an oblique direction of approaching the water tank 109, the air current reaches the water in the water tank 109 and thus, there is a concern that a ripple will be formed on the water surface, thereby bring about instability in the water surface and generating bubbles.

Note that the ultrasound inspection apparatus 100A may cause the air knife generators 118A and 118B to be actuated according to the scanning direction of the work 106. The ultrasound inspection apparatus 100A causes the air knife generator 118A to be actuated such that the air knife current 121A is blown out in a case where the work 106 is scanned from right to left in the drawing. The ultrasound inspection apparatus 100A causes the air knife generator 118B to be actuated such that the air knife current 121B is blown out in a case where the work 106 is scanned from left to right in the drawing. In this manner, it is possible to reduce an amount of consumption of the high-pressure gas and it is possible to maintain the stability of the water surface in the water tank 109 without a ripple.

Third Embodiment

Unlike the first embodiment, in the ultrasound inspection apparatus 100B of a third embodiment, the work 106 is fixed and the array probe 107 moves along the XYZ axes. An advantageous point of the ultrasound inspection apparatus of the third embodiment is that the ultrasound inspection apparatus can take a small space because the work 106 is fixed.

FIG. 5 is a view of a schematic configuration showing a part of an ultrasound inspection apparatus 100B according to the third embodiment. The same reference signs are assigned to the same components as those in the ultrasound inspection apparatus 100 of the first embodiment shown in FIG. 1.

In the ultrasound inspection apparatus 100B of the third embodiment, the array probe 107 and the casing 108 are surrounded by the water tank 109. A pan 240 is provided under the water tank 109. The pan 240 receives water overflowing from the water tank 109. A drainage tube 241, through which water is drained, is connected to the pan 240. The water tank 109 is supported by the adjustment screws 131A, 131B, and 131C, and is attached to the casing 108 of the array probe 107 by being fitted to the casing to the extent that the water tank moves vertically in a smooth manner without rattling. In addition, the casing 108 of the array probe 107 penetrates through the pan 240 and is fixed to a pan fixing base 242. A gap between the pan 240 and the casing 108 of the array probe 107 is sealed with a caulking agent or the like such that water does not leak through the gap.

The pan 240 is disposed on the pan fixing base 242. The pan fixing base 242 is disposed on a two-axis gonio stage 205. The two-axis gonio stage 205 adjusts the inclination of the array probe 107 in the XY directions.

The two-axis gonio stage 205 is movable in the Z-axial direction by the Z-axial direction scanning means 202. The two-axis gonio stage 205 is movable in the X-axial direction by the X-axial direction scanning means 204. The two-axis gonio stage 205 is movable in the Y-axial direction by the Y-axial direction scanning means 201. Accordingly, since the ultrasound inspection apparatus 100B of the third embodiment can scan the array probe 107 in the directions of XYZ axes, the work 106 (not shown) is fixed and it is possible to reduce a plane-project area of the ultrasound inspection apparatus 100B. Since the work 106 is fixed and is probed with the ultrasonic wave, the ultrasound inspection apparatus 100B can acquire a more accurate ultrasonic image by reducing the vibration of the work 106.

FIG. 6 is an enlarged view showing a configuration in the vicinity of the array probe 107 and an operation thereof according to the third embodiment.

The water supplied from the water supply tube 111 overflows the water tank 109, is received by the pan 240, and becomes drainage water 245. The drainage water 245 is drained via the drainage tube 241. In such a configuration, the X-axial direction scanning means 204, the Y-axial direction scanning means 201, and the Z-axial direction scanning means 202 are not wet in water.

Note that the water drained via the drainage tube 241 may be circulated by reflux in the pump 130. In this manner, it is possible to reduce an amount of water used.

The height and parallelization of the water tank 109 can be adjusted separately from the height and parallelization of the array probe 107, by the adjustment knobs 113A and 113B and the adjustment knob 113C disposed on a side opposing to the array probe 107. The adjustment knob 113A and the adjustment screw 131A are connected to each other via a seal bearing 132A. The adjustment knob 113B and the adjustment screw 131B are connected to each other via a seal bearing 132B. The adjustment knob 113C and the adjustment screw 131C are connected to each other via a seal bearing 132C. The seal bearings 132A, 132B, and 132C are provided so as to prevent water from leaking from the pan 240. Turning of the adjustment knobs 113A, 113B, and 132C causes the water tank 109 to move upward and downward along the outer edge of the array probe 107.

The water supplied from the water supply tube 111 is supplied to the water tank 109 via the water supply port 110. The water overflowing the top edge of the water tank 109 is stored as the drainage water 245 in the pan 240. The drainage water 245 is drained to the outside via a drainage port 244 and the drainage tube 241.

The ultrasound inspection apparatus 100B of the third embodiment includes a vacuum suction mechanism 250. The vacuum suction mechanism 250 includes an O-ring 251 and the work 106 is stopped by performing vacuum suction on a surface opposite to the inspection surface of the work 106. In a vacuum suction method, the water tank 109 and the array probe 107 further approach the inspection surface, compared to a method in which the work 106 is mechanically stopped.

The ultrasound inspection apparatus 100B of the third embodiment performs scanning as follows.

As shown in FIG. 6, an inspector, first, performs chucking of the work 106 with the inspection surface thereof facing downward, using the vacuum suction mechanism 250. As another method different from the above method, a method of holding the work 106 by performing vacuum suction on the top surface of the work, or a method of holding the work 106 from the side surfaces by pressing a material having a high friction coefficient against side surfaces of the work are considered. In this manner, the inspection surface of the work 106 horizontally faces downward.

Next, the inspector causes the array probe 107 to move to a position below the inspection surface (inspection region) of the work 106, using the X-axial direction scanning means 204 and the Y-axial direction scanning means 201.

Next, the pump 130 supplies water to the water tank 109 through the water supply tube 111 and the water supply port 110 and time is taken for the water 117 to overflow the top edge of the water tank 109. In this manner, it is possible for the liquid surface to be higher than the top edge of the water tank 109 due to the surface tension of water. The pump 130 supplies water to the extent that no ripple is formed on the water surface and the water surface appears to be substantially a still-water surface. This is done so as to prevent an ultrasonic wave generated from the array probe 107 from being readily reflected from bubbles generated when a ripple is formed on the water surface.

FIG. 6 is an enlarged view showing a configuration in the vicinity of the array probe 107 and an operation thereof according to the third embodiment, in which the water 117 overflows the edge of the water tank 109.

As shown in FIG. 6, the water surface of the water 117 is raised by the height h from the top edge of the water tank 109 due to the surface tension.

In this state, the array probe 107 and the water tank 109 are lifted by using the Z-axial direction scanning means 202 until the liquid surface of the water 117 reaches the inspection surface. At this time, when the position of the top edge of the water tank 109 is too high or reaches the inspection surface of the work 106 by being inclined, the distance (height) and the inclination of the water tank 109 with respect to the inspection surface are adjusted by using the adjustment knobs 113A, 113B, and 113C. In this manner, it is possible to perform height adjustment and parallelization of the top edge of the water tank 109.

As shown in FIG. 6, the signal cable 115 is electrically connected to the array probe 107. The signal cable 115 passes through the inside of the pan fixing base 242 or the like, so as not to interfere with the movement of the X-axial direction scanning means 204, the Y-axial direction scanning means 201, the Z-axial direction scanning means 202, and the two-axis gonio stage 205. The water overflowing the top edge of the water tank 109 is received by the pan 240. A space between the array probe 107 and the casing 108 and a space between the casing 108 and the pan fixing base 242 are filled with caulking or the like, thereby preventing short due to wetting of the signal cable.

Hereinafter, a method of inspection will be described with reference to FIGS. 5 and 6.

The inspector causes an ultrasonic wave to be generated from the array probe 107 connected to the signal cable 115 and focuses the ultrasonic wave on the inspection surface of the work 106. The Z-axial direction scanning means 202 is used to concentrate the ultrasonic wave to the focus. At this time, a height of the water tank 109 is also adjusted appropriately by using the adjustment knobs 113A, 113B, and 113C, depending on the movement of the Z-axial direction scanning means 202 such that the top edge of the water tank 109 does not collide with the work 106, or the surface of the water 117 is not separated from the inspection surface. The two-axis gonio stage 205 is adjusted such that time taken for an echo signal reflected from the inspection surface of the work 106 to return is uniformly taken for the array probe 107 in the longitudinal direction, and thereby parallelization of the array probe 107 is performed with respect to the inspection surface of the work 106. In this manner, the array probe 107 can probe a surface parallel to the inspection surface of the work 106 with the ultrasonic wave.

Then, using the Z-axial direction scanning means 202, the inspector focuses the array probe 107 on a predetermined depth at which the inspection of the work 106 needs to be performed. At this time, the inspector also adjusts a height of the water tank 109 appropriately by using the adjustment knobs 113A, 113B, and 113C, depending on the movement of the Z-axial direction scanning means 202 such that the top edge of the water tank 109 does not collide with the work 106, or the surface of the water 117 is not separated from the inspection surface. Further, the height adjustment and the parallelization of the water tank 109 are performed by using the adjustment knobs 113A, 113B, and 113C such that a height H is secured between the edge of the water tank 109 and the inspection surface. In this manner, the ultrasound inspection apparatus 100B can inspect a layer at a predetermined depth from the inspection surface of the work 106.

As shown in FIG. 6, the height H of the inspection surface of the work 106 with respect to the top edge of the water tank 109 is equal to or smaller than a height h of the water surface raised from the top edge of the water tank 109 due to the surface tension. In this manner, in the state in which the water surface appears to be substantially the still-water surface without a ripple, it is possible for the liquid surface of the water 117 to come into contact with the inspection surface and thus, it is possible to reduce an occurrence of bubbles. Here, the height H is set to be greater than 0 mm and 2 mm or less. With the operations described above, the adjustment of the array probe 107 and the water tank 109 is completed.

It is desirable that a surface of the top edge of the water tank 109 facing the inspection surface is formed of a material having poor wettability with respect to water or a material subjected to surface processing so as to have poor wettability, because the height h of the water surface raised from the top edge of the water tank 109 is increased due to the surface tension.

Next, the ultrasound inspection apparatus 100B causes the array probe 107 to move to a starting point and scanning is started.

First, the X-axial direction scanning means 204 horizontally scans the array probe 107 in the X direction by sending the array probe in the X direction. The X-axial direction scanning means 204 (horizontal scanning means) scans the array probe 107 in the horizontal (X-axial) direction, with the liquid surface coming into contact with the inspection surface of the work 106 due to the surface tension of the water stored in the water tank 109.

When scanning of one line in the X direction is completed, the Y-axial direction scanning means 201 sends the array probe 107 by an amount of a length of the array probe 107 in the longitudinal direction. The Y-axial direction scanning means 201 (horizontal scanning means) sends the work 106 in the horizontal (Y axis) direction, with the liquid surface coming into contact with the inspection surface of the work 106 due to the surface tension of the water stored in the water tank 109.

Next, the X-axial direction scanning means 204 sends the array probe 107 in a direction opposite to the previous scanning in the X direction. The X-axial direction scanning means 204 (horizontal scanning means) scans the array probe 107 in the horizontal direction, with the liquid surface coming into contact with the inspection surface of the work 106 due to the surface tension of the water stored in the water tank 109.

The ultrasound inspection apparatus 100B repeats the scanning procedures and scans the inspection region. After the completion of the scanning of the inspection region, scanning is again performed by focusing on a layer of the work 106 at another depth in accordance with the above procedure as necessary. In this manner, the ultrasound inspection apparatus 100B can scan the work 106 having the multi-layer structure.

The scanning of the array probe 107 by the X-axial direction scanning means 204 and Y-axial direction scanning means 201 is performed at a speed which is slow to the extent that the water is not spilt out due to inertia and no air enters the space between the inspection surface of the work 106 and the water tank 109, and the speed is controlled to become high and low in a smooth manner. In this manner, the bubbles are prevented from being put on the inspection surface so as not to be an obstacle to the irradiation and reception of the ultrasonic wave by the array probe 107.

Modification Example

The present invention is not limited to the embodiments described above, and includes various types of modification examples. For example, the embodiments described above are described in detail so as to easily construe description of the present invention, and do not need to be limited to a combination of the entire configurations described above. It is possible to replace a part of a configuration of a certain embodiment with another configuration of another embodiment, and it is possible to add a configuration of a certain embodiment to another configuration of another embodiment. In addition, to a part of a configuration of each of the embodiment, it is possible to perform addition, removal, or replacement of another configuration.

According to the respective embodiment, a control line or an information line is shown when the line is considered to be necessary in description, and the entirety of the control lines and the information lines in a product does not need to be shown. In practical, it may be considered that almost all of the configurations are connected one another.

REFERENCE SIGNS LIST 100, 100A, 100B ultrasound inspection apparatus
101, 201 Y-axial direction scanning means (horizontal scanning means)
102, 202 Z-axial direction scanning means (height adjusting mechanism, distance adjusting mechanism)
103 stage (probe holding mechanism)
104A, 104B, 204 X-axial direction scanning means (horizontal scanning means)
105 work holder (subject holding mechanism)
106 work (subject)
107 array probe
108 casing
109 water tank (tank)
111 water supply tube
112A, 112B fixing screw (tilting-amount adjusting mechanism)
113A, 113B, 113C adjustment knob (water tank-tilting/height adjusting mechanism, distance adjusting mechanism)
114 connector
115 signal cable
116 arm (probe holding mechanism)
117 water
118A, 118B air knife generating device (current generating device)
119A, 119B high-pressure gas tube 120A, 120B high-pressure supply port
121A, 121B air knife current
130 pump
131A, 131B, 131C adjustment screw (water-tank tilting/height adjusting mechanism)
132A, 132B, 132C seal bearing
205 two-axis gonio stage (probe holding mechanism)
240 pan
241 drainage tube
242 pan fixing base
250 vacuum suction mechanism

The invention claimed is:

1. An ultrasound inspection apparatus comprising:
   a subject holding mechanism that horizontally holds a subject with a planate inspection surface thereof facing downward;
   a linear array probe that probes the subject with an ultrasonic wave;
   a tank in which the array probe is immersed in a liquid that causes ultrasonic waves to be propagated;
   a probe holding mechanism that holds the array probe and the tank such that the array probe faces an underside of the inspection surface of the subject;
   horizontal scanning means that horizontally scans the subject and/or the array probe, with a liquid surface coming into parallel contact with the inspection surface of the subject due to surface tension of a liquid stored in the tank;
   a height adjusting mechanism that adjusts a relative height of the tank and a relative height of the probe holding mechanism with respect to the subject; and
   a tilting-amount adjusting mechanism that adjusts an amount of tilting of the array probe.

2. The ultrasound inspection apparatus according to claim 1, further comprising:
   an air-current generator that is provided to be parallel to the array probe and generates a sheet-shaped air current in a direction of being away from the tank.

3. The ultrasound inspection apparatus according to claim 1,
   wherein the subject holding mechanism holds the subject from an upper side thereof by vacuum suction.

4. The ultrasound inspection apparatus according to claim 1,
   wherein, when the subject and/or the array probe is horizontally scanned, an interval between the inspection surface of the subject and a top edge of the tank is longer than 0 mm and 2 mm or shorter.

5. The ultrasound inspection apparatus according to claim 1, further comprising:
   a pump or a flow-rate regulating mechanism that supplies a liquid at a flow rate at which no ripple is formed on a liquid surface in the tank.

6. The ultrasound inspection apparatus according to claim 1,
   wherein the horizontal scanning means horizontally scans the subject and/or the array probe at a speed at which no air enters a space between the inspection surface of the subject and the array probe.

7. The ultrasound inspection apparatus according to claim 1, wherein the array probe is fixed.

8. The ultrasound inspection apparatus according to claim 7, wherein the subject holding mechanism is movable.

* * * * *